United States Patent [19]

Ehara

[11] Patent Number: 4,884,435
[45] Date of Patent: Dec. 5, 1989

[54] ODOR IDENTIFYING APPARATUS AND METHOD

[76] Inventor: Katsuo Ehara, 4-18-6, Kamisaginomiya, Nakano, Nakano-Ku, Tokyo-yo, Japan

[21] Appl. No.: 272,465
[22] Filed: Nov. 17, 1988

[30] Foreign Application Priority Data

Nov. 17, 1987 [JP] Japan ............................... 62-288574

[51] Int. Cl.⁴ ........................................... G01N 31/00
[52] U.S. Cl. ........................................... 73/23; 422/83
[58] Field of Search ............... 73/23, 27; 340/632, 340/634; 422/83, 98

[56] References Cited

U.S. PATENT DOCUMENTS

| | | | |
|---|---|---|---|
| 4,244,712 | 1/1981 | Tongret | 55/124 |
| 4,563,893 | 1/1986 | Tanyolac et al. | 73/23 |
| 4,724,008 | 2/1988 | Bell et al. | 204/432 |
| 4,770,027 | 9/1988 | Ehara et al. | 73/23 |

Primary Examiner—Hezron E. Williams
Attorney, Agent, or Firm—Jones, Tullar & Cooper

[57] ABSTRACT

An odor identifying apparatus comprising a gas sensor unit including at least two sensors having different characteristics for simultaneously detecting odorous components arising from a sample and outputting detection signals, a display device for displaying detection results from the sensor unit as a single output signal, and an ozone gas generator for supplying ozone gas into a chamber in which the sample is placed. An odor identifying method is also disclosed which identifies odorous components by using this apparatus.

14 Claims, 4 Drawing Sheets

ODOR IDENTIFYING APPARATUS AND METHOD

FIELD OF THE INVENTION

The present invention relates to an odor identifying apparatus and method for detecting and identifying various odors.

DESCRIPTION OF THE PRIOR ART

The necessity often arises in the food industry and perishable food handling business to carry out quality control of various foods based on their flavors. Conventionally, such quality control takes the form of an organoleptic test by a panel of specialists or, where a stricter measurement is required, employs a gas analyzer such as a gas chromatograph or a gas chromatograph-mass spectrometer.

The organoleptic test by a panel of specialists, however, inevitably produces measurement results influenced by differences among the individual panelists. It also has various problems such as of considerable cost and time necessary for training personnel to become specialists. The method of measuring odorous components with a gas analyzer lacks accuracy in direct identification of odorous components since the intensity of odor perceived by humans does not always agree with the amount of odorous components detected by the analyzer. Furthermore, the analyzer is a sophisticated machine troublesome to operate and requiring skill and time to use it in measurement. Besides, the analyzer itself is costly.

SUMMARY OF THE INVENTION

Having regard to the state of the art noted above, the object of the present invention is to provide an odor identifying apparatus which is free from the disadvantages of the prior art, capable of comparing and identifying various odors (volatile substances) easily, speedily and with high precision, and yet compact in construction and inexpensive. The present invention also intends to provide an odor identifying method utilizing this apparatus.

In order to achieve the above object, an odor identifying apparatus according to the present invention comprises a gas sensor unit including at least two sensors having different characteristics for simultaneously detecting odorous components arising from a sample and outputting detection signals, and display means for displaying detection results from the sensor unit as a composite output signal, wherein an ozone gas generator is provided for supplying ozone gas into a chamber in which the sample is placed.

An odor identifying method according to the present invention comprises the steps of placing a sample on a sample holder, simultaneously detecting odorous components arising from the sample with at least two gas sensors included in a gas sensor unit and having different characteristics, outputting detection results, and displaying the output signals at display means as a composite output signal, wherein, prior to detecting the odorous components, ozone gas generated by an ozone gas generator is supplied into a chamber in which the sample is placed.

In the odor identifying apparatus according to the present invention, the characteristics of odorous components are picked up as an output ratio between a plurality of, for example, two, gas sensors, and detection results provided by the gas sensors are displayed as the trace of a single output signal. An ozone gas generator is disposed in a chamber in which a sample is placed, for generating ozone gas after the measurement. Ozone is used for the purpose of cleaning not only the sensor unit but also the odorimetric chamber. Consequently, the sensor outputs are easily and quickly adjusted to zero to allow a next measurement to be taken without influences of the residual gas. The odor identifying apparatus thus allows the number of measurements to be increased while maintaining high measuring precision, thereby enabling efficient measurement operations. Besides, this odor identifying apparatus is compact and inexpensive since it is constructed without incorporating any complicated mechanisms.

In effecting quality control of products of the same kind by means of the odor identifying apparatus and method according to the present invention, for example, measurement is taken of the extent of deviation from quality characteristics of standard products determined in advance. This feature realizes great utility in that the qualities of the products subjected to the measurement may be judged promptly and reliably.

In particular, the odor identifying apparatus according to the present invention directly detects odors of a sample by means of the sensors instead of employing the sampling method as practiced with the gas chromatograph and gas chromatograph-mass spectrometer in which odors of a sample are collected first and are then introduced to an injector. The direct odor detection in the apparatus of the present invention assures a high degree of reliability and reproducibility with regard to measuring precision and results of measurement.

Furthermore, the identification of odorous components is effected without involving contact with the sample according to the present invention. This feature protects the sample from damage and minimizes contamination by the sample of the apparatus per se for facility of its maintenance.

Other advantages of the odor identifying apparatus and method according to the present invention will be apparent from the detailed description of the preferred embodiment.

BRIEF DESCRIPTION OF THE DRAWINGS

The drawings illustrate an odor identifying apparatus according to the present invention, in which.

DETAILED DESCRIPTION OF THE PREFERRED EMBODIMENT

An odor identifying apparatus and method embodying the present invention will be described in detail hereinafter with reference to the drawings.

Figure 1:
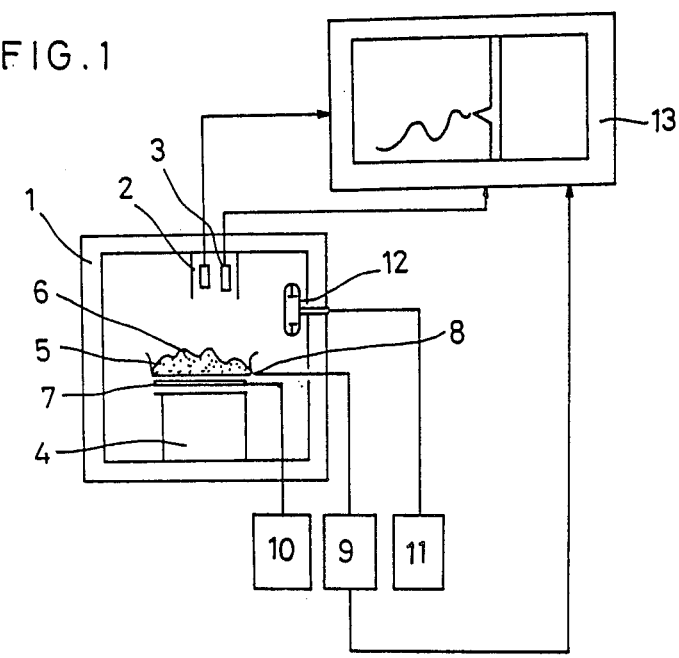
FIG. 1 is a block diagram of the odor identifying apparatus.
Figure 2:
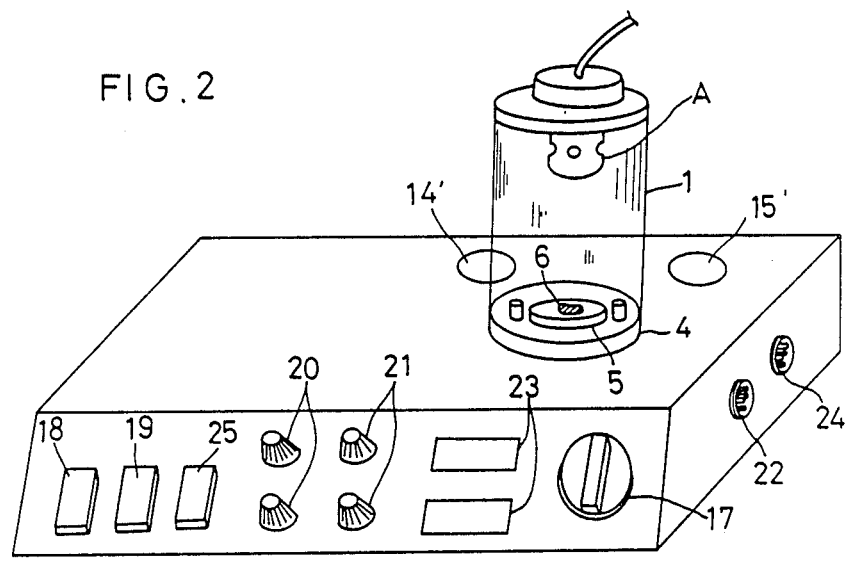
FIG. 2 is a perspective view of a main body of the odor identifying apparatus.

FIG. 1 shows a constructional outline of the odor identifying apparatus, and FIG. 2 an outward appearance of a main body of the apparatus (i.e. excluding a display device).

The odor identifying apparatus comprises a chamber 1 housing a sample holder including a vessel 5 and a table 4, and a gas sensor unit A including two gas sensors 2 and 3 having different characteristics. The apparatus further comprises an X-Y recorder 13 acting as display device for displaying detection results from the gas sensor unit A as a composite output signal, and driving power sources 10 and 11 connected, respectively, to a heater 7 mounted inside the table 4 and to an ozone gas generator 12 for adjusting the output of the gas sensor unit A to zero.

As shown in FIG. 2, the chamber 1 is formed of removable transparent glass to allow visual observation from outside of a sample placed in the chamber 1. The chamber 1, however, need not be transparent but will serve the purpose if formed of a material inadsorptive to odorous components. Materials having this property include tetrafluoroethylene resin such as Teflon, and glass. It is desirable for the sample holder and an outer frame of the gas sensor unit A, besides the chamber 1, to be formed of the materials inadsorptive to odorous components to enhance measuring precision.

Figure 3:
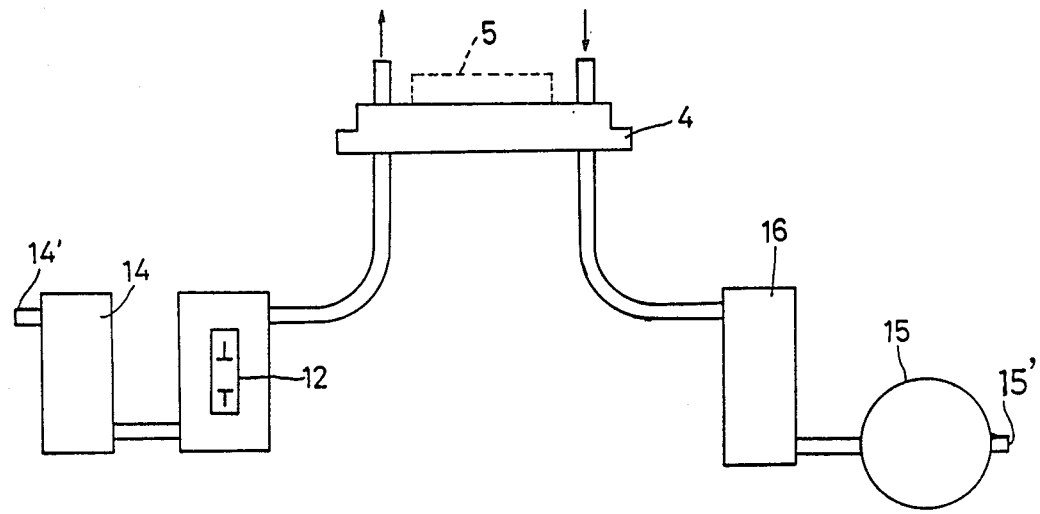
FIG. 3 is a block diagram of an ozone gas injection line used with the apparatus of FIG. 2.

The ozone gas generator 12 need not be disposed inside the chamber 1 but ozone gas may be introduced into the chamber 1 from outside as shown in FIGS. 2 and 3.

The heater 7 mounted inside the table 4 is for heating sample 6 placed on the vessel 5. The heater 7, although not an essential component of the apparatus, may be used to heat a sample having only slight odorous components and promote their evaporation in preparation for the measurement. Thus, the heater 7 has the effect of substantially enhancing sensitivity of this apparatus. When the sample is heated slowly, volatile substances evaporate at low temperatures whereas substances that are not volatile evaporate at high temperatures. Consequently, different odorous components, or component ratios, occur from the sample at low temperatures and at high temperatures, which facilitates identification of the sample. In other words, the entire shape of a curve displayed on the X-Y recorder 13 may be seen as identification data.

Figure 7:
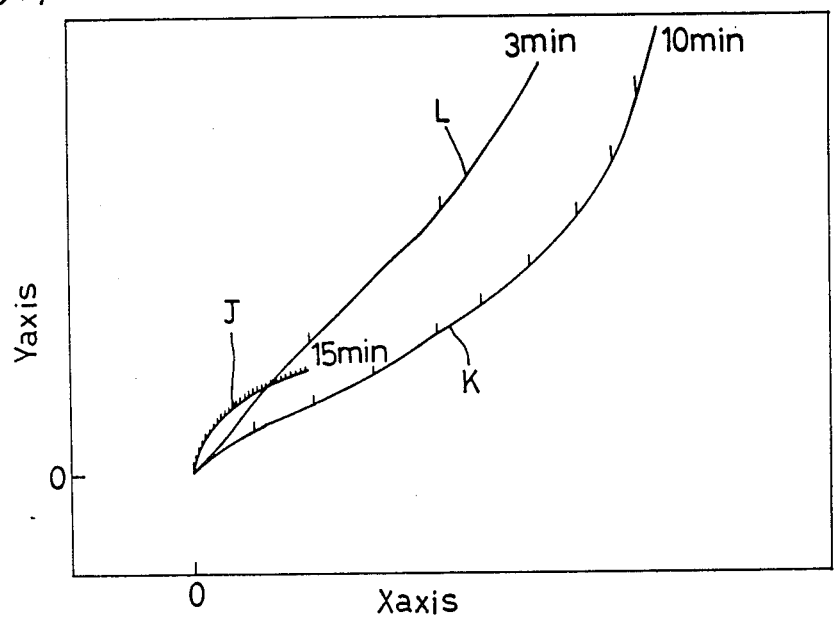
FIG. 7 is a graph showing measurement data of two kinds of tea powder and coffee powder where a time factor is incorporated.

Furthermore, this apparatus may be used also as thermal gas analyzer for EGD or evolved gas detection as illustrated in FIG. 7 which will be described later. As seen from FIG. 1, instead of applying output of one of the sensors in describing a line on the X-Y recorder 13, a thermocouple 8 for measuring sample temperatures may be connected through an electric converter 9 to the X-Y recorder 13 for describing a line. Then, voltage of the thermocouple 8 is input to the X-axis. This construction allows grasp of the odorous components resulting from heating.

The chamber 1 defines an opening for putting sample 6 into and taking it out of the chamber 1. This opening preferably has a tight-sealing construction to seal the interior of the chamber 1 from ambient air. For example, an inner lid may be provided with a packing.

The ozone gas generator 12 may comprise a lamp or the like for generating ultraviolet rays (having a wavelength of 2537Å, for example). Ion atmosphere may be used instead, which is generated from a needle electrode connected to a high voltage source, or other devices may be employed for the purpose of this invention. The ozone gas generator 12 allows the sensor output to be set to zero with ease and speed, which realizes a quick, stable and accurate measurement. The use of ozone gas generator 12 provides the further advantage of cleaning the chamber interior. The ozone gas generation by the ozone gas generator 12 may be followed by injection into the chamber 1 of clean air having flowed through activated carbon or an inert gas such as argon gas or nitrogen gas, which step is taken for a fixed period with the ozone gas generator 12 turned off.

Figure 4:
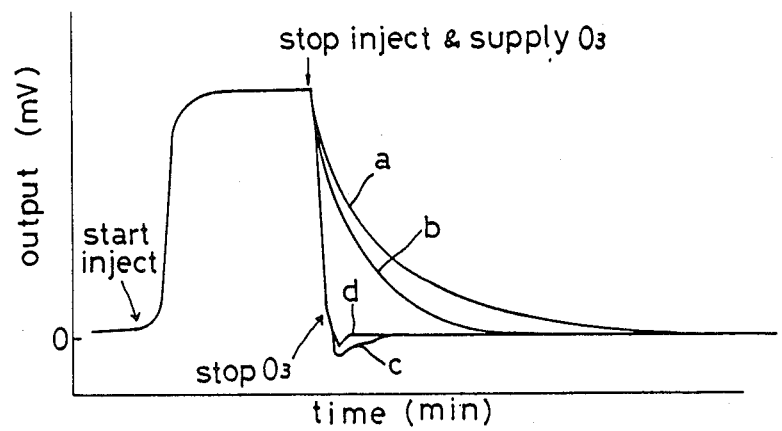
FIG. 4 is a graph showing injection of gases for setting sensor outputs to zero.

As shown in FIG. 4 in particular, clean air having flowed through activated carbon is injected into the chamber 1 by means of a clean gas injector after the ozone gas generation, whereby the sensor output is set to zero with increased speed. In FIG. 4, reference a represents a case where the gas is not introduced after measurement, reference b represents a case where clean air having flowed through activated carbon is introduced after a measurement, reference c represents a case where ozone gas is generated and introduced after a measurement, and reference d represents a case where ozone gas is introduced and then clean air having flowed through activated carbon is introduced after a measurement.

As shown in FIG. 3, the clean gas injector may comprise a pump 15 which injects clean air into the chamber 1 through a filter 14 provided below the table 4 and including activated carbon and a dehydrating agent. In this case, the ozone gas generator 12 is stopped and the pump 15 is actuated whereby fresh air is allowed to flow from an intake opening 14' through the filter 14, and discharged through an exhaust opening 15'. An ozone gas decomposing filter 16 is provided for preventing an adverse effect resulting from the passage of ozone gas through the pump 15. Reference number 17 in FIG. 2 indicates a timer switch for setting an ozone gas generating time, number 18 indicates a power switch, number 19 indicates a measurement start switch, number 20 indicates zero adjustment knobs connected to the respective sensors, number 21 indicates a range switching knob, number 22 indicates a sensor unit connector, number 23 indicates digital display panels for displaying outputs of the respective sensors, number 24 is an X-Y recorder connector, and number 25 indicates a power switch for the heater.

The odor identifying method using the foregoing apparatus will be described next.

First, the ozone gas generator 12 is actuated to generate ozone gas, which is introduced into the chamber 1. Next, the pump 15 is actuated to introduce clean air into the chamber 1, completely remove the ozone gas from the chamber 1 and clean the chamber interior. Thereafter the sensor outputs are adjusted to zero by means of the zero-point adjusting knob 20. Then a suitable amount of sample 6 is placed in the vessel 5 and the chamber 1 is sealed. The heater 7 is used to heat the sample 6 as appropriate if the sample 6 is a substance that does not readily give off odorous components.

The odorous components produced from the sample 6 are detected by the two gas sensors 2 and 3 having different characteristics. The results of detection are displayed and recorded by the X-Y recorder 13. The two gas sensors 2 and 3 detect the odorous components independently of each other, which result in biased graphs reflecting the nature of the odorous components.

Thus, a quality dispersion in products of the same kind may be determined with ease and products falling outside a quality control range found easily and positively by measuring the odorous components of a standard sample and recording these odorous components in the X-Y recorder 13 together with the control range in advance, which range is fixed with reference to standard sample data. A device may readily be provided for automatically giving an alarm when a product checked is outside the control range.

The device for displaying the detection results from the gas sensor unit as a single output signal may comprise, instead of the X-Y recorder, a CPU for comparing the detection results from the two sensors and processing the biases provided by the respective sensors. The results provided by the CPU may, for example, be displayed on a CRT display.

Experiments have been conducted on the identifying apparatus and method of the present invention in which the odorous components of various samples are detected. The particulars of these experiments will be described now.

Experiment 1

Tea, instant coffee powder and coffee bean powder were used as samples, and their odorous components were detected by the two sensors. The X-axis sensor comprised a semiconductor gas sensor of the sintered type manufactured by adding an alkaline earth metal oxide (CaO) to tin dioxide ($SnO_2$). The Y-axis sensor comprised a film type semiconductor gas sensor manufactured by depositing tin dioxide ($SnO_2$) on a heat-resistant insulating substrate.

The X-axis sensor was particularly sensitive to gases of alcohol, aldehyde and other oxygen-containing organic compounds. The Y-axis sensor was non-selective and was sensitive to all types of gas.

Figure 5:
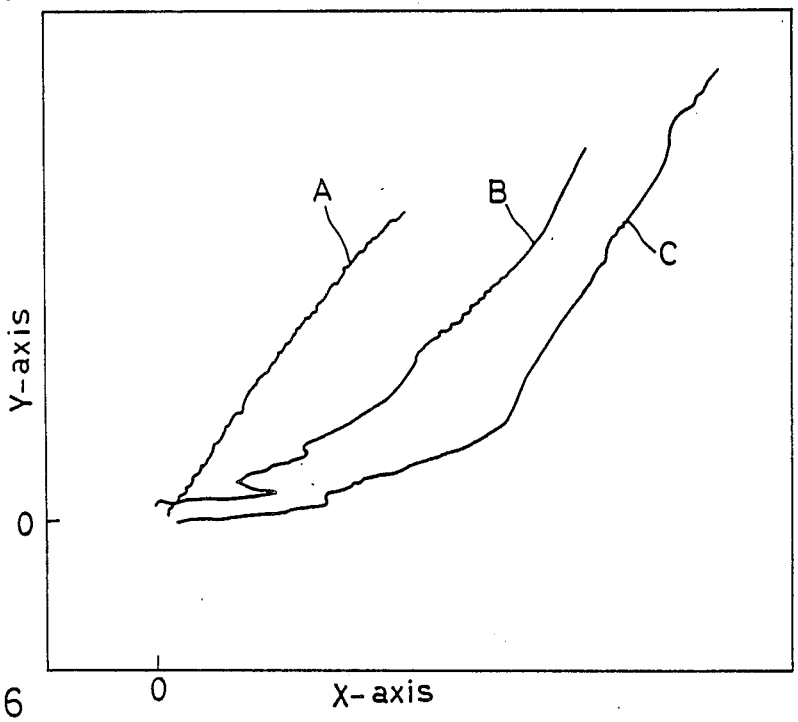
FIG. 5 is a graph showing measurement data of tea, instant coffee powder and coffee bean powder.

FIG. 5 shows results of the measurement obtained from the combination of the above sensors.

In FIG. 5, reference A represents measurement data of tea powder, reference B measurement data of instant coffee powder, and reference C measurement data of coffee bean powder.

It will be seen that each sample is identifiable from the unique curve it describes. In particular, there is a clear distinction between instant coffee powder and coffee bean powder though they are both coffee products.

Experiment 2

Figure 6:
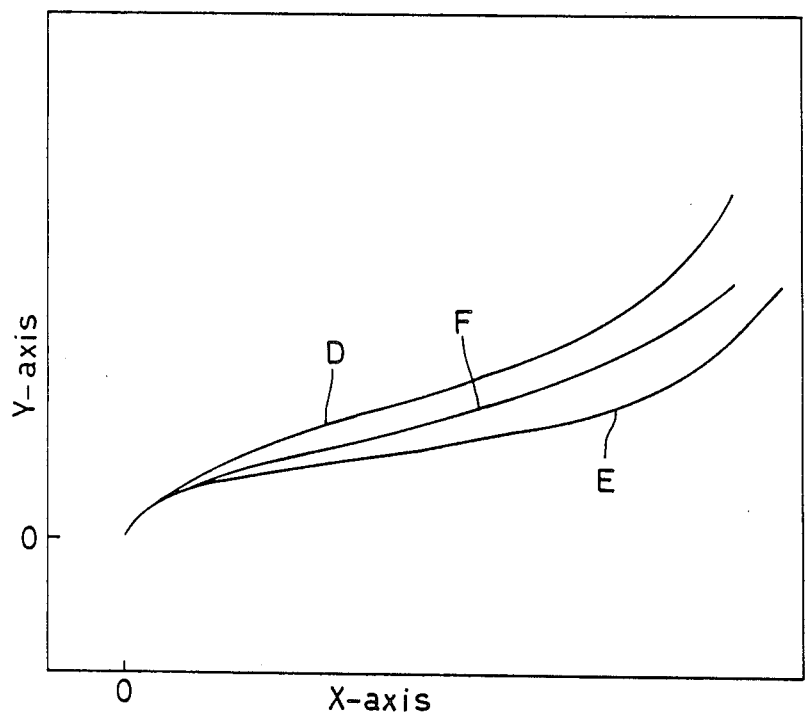
FIG. 6 is a graph showing measurement data of Geraniol, 1-Citronellol and a 1:1 mixture of Geraniol and 1-Citronellol.

This experiment employed Geraniol, 1-Citronellol and a 1:1 mixture of the two substances as samples. The results of the measurement are shown in FIG. 6 as referenced D, E and F, respectively.

It will be seen that these samples may also be clearly identified.

Experiment 3

This experiment employed two types of tea powder, i.e. Lipton's Orange and Twining's Bergamot, and coffee powder. The results of the measurement are shown in FIG. 7 as referenced J, K and L, respectively. The measurements were taken by incorporating a time factor in this case. Reference J corresponds to 15 minutes from start till finish of the measurement, reference K to 10 minutes, and reference L to 3 minutes. It is clear from the measurement results that there are considerable differences in time dependence among the two different types of tea powder and coffee powder with respect to generation of odorous components.

Thus, the odor identifying apparatus according to the present invention is adaptable as an identifying apparatus of increased sensitivity which allows grasp of overall shapes by adding the time factor.

Experiment 4

This experiment employed cigarette filters before and after use as samples and measured odorous components produced through heating. The results are shown in FIG. 8.

Figure 8:
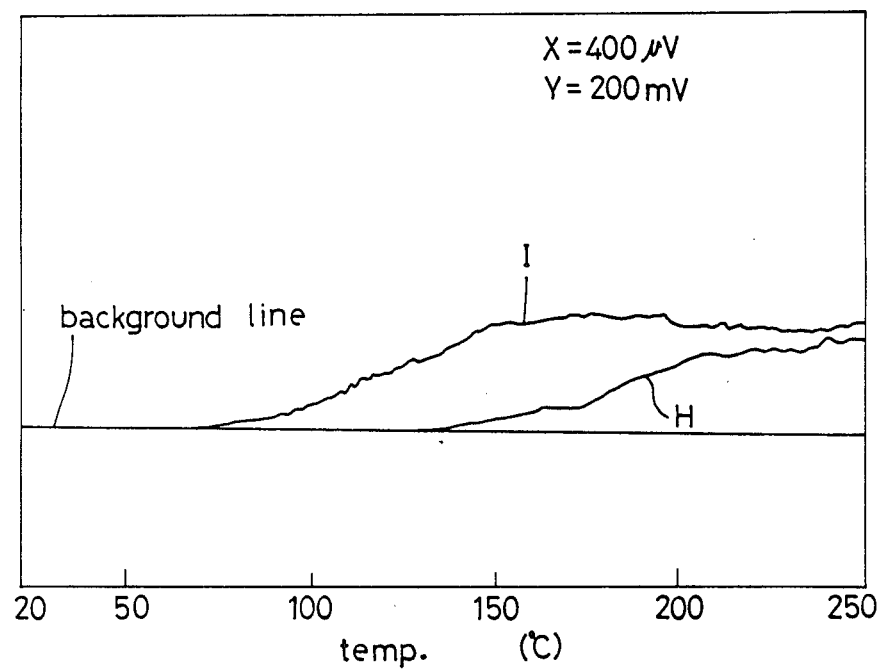
FIG. 8 is a data graph showing EGD characteristics derived from heating used and unused cigarette filters.

In FIG. 8, reference H represents detection data relating to the unused cigarette filter, and reference I detection data relating to the used filter. The graph clearly shows that tar and the like produced through smoking had been absorbed in the used filter and began to evaporate as odorous components at a relatively low temperature below 100° C.

Apart from the sensors employed in the above embodiment, the following various sensors may be used in combination for measuring odorous substances:

(1) a sintered type sensor manufactured by adding lanthanum trioxide ($La_2O_3$) or other rare earth oxide as well as an alkaline earth metal oxide to tin dioxide for detecting alcohol, aldehyde, ketone, acid, ester and other oxygen-containing organic compounds, (2) a film type sensor having tin dioxide and zinc oxide as main components for detecting hydrogen sulfide, mercaptan, sulfide and other sulfur-containing organic compounds, (3) a sintered type sensor manufactured by adding palladium or the like to tin dioxide for detecting ammonia, amine and other nitrogen-containing organic compounds, and (4) a sintered type sensor manufactured by controlling surface activity of tin dioxide or adding a noble metal catalyst to tin dioxide for detecting benzene, xylene, methylcyclohexane, hexane and other unsaturated or saturated hydrocarbons.

While two sensors having different characteristics are used in the foregoing embodiment, the number of sensors may be increased according to purpose. Measuring precision may be enhanced for a higher identifying performance by using an operating device such as a CPU for processing the sensor outputs and allowing composite display and recording of these outputs.

Further, in the foregoing embodiment only solid samples are used as objects to be identified but the samples may also be in fluid form such as liquid.

The odor identifying apparatus and method according to the present invention may be used for various purposes, such as freshness rating of perishable foods, standard setting for shipment of various food, quality control of cosmetics, and flavoring. In other words, the present invention has a very wide range of application, and may be used in any fields of industry that handle volatile substances.

What is claimed is:

1. An odor identifying apparatus comprising: a gas sensor unit including at least two sensors having different characteristics for simultaneously detecting odorous components arising from a sample and outputting detection signals; and display means for displaying detection results from said sensor unit as a single composite output signal representing a ratio between outputs from said respective gas sensors.

wherein an ozone gas generator is provided for supplying ozone gas into a chamber in which said sample is placed.

2. An odor identifying apparatus as claimed in claim 1, further comprising a clean gas injector for supplying a clean gas into said chamber.

3. An odor identifying apparatus as claimed in claim 1, further comprising a sample holder for supporting said sample, said sample holder including heating means.

4. An odor identifying apparatus as claimed in claim 1, wherein said display means is an X-Y recorder.

5. An odor identifying apparatus as claimed in claim 4, wherein said X-Y recorder gives a display by incorporating a time factor.

6. An odor identifying method comprising the steps of:
  placing a sample on a sample holder;
  simultaneously detecting odorous components arising from said sample with at least two gas sensors included in a gas sensor unit and having different characteristics, and outputting detection results; and
  displaying said output signals at display means as a single composite output signal representing a ratio between outputs from said respective gas sensors,
  wherein, prior to detecting said odorous components, ozone gas generated by an ozone gas generator is supplied into a chamber in which said sample is placed.

7. An odor identifying method as claimed in claim 6, wherein said odorous components are detected by said gas sensors while heating said sample with heating means included in said sample holder.

8. An odor identifying method as claimed in claim 6, wherein a clean gas is supplied by a clean gas injector into said chamber after ozone gas is generated by said ozone gas generator.

9. An odor identifying method as claimed in claim 6, wherein said display means is an X-Y recorder.

10. An odor identifying method as claimed in claim 9, wherein said X-Y recorder gives a display be incorporating a time factor.

11. An odor identifying apparatus as claimed in claim 2, further comprising a sample holder for supporting said sample, said sample holder including heating means.

12. An odor identifying apparatus as claimed in claim 2, wherein said display means is an X-Y recorder.

13. An odor identifying method as claimed in claim 7, wherein a clean gas is supplied by a clean gas injector into said chamber after ozone gas is generated by said ozone gas generator.

14. An odor identifying method as claimed in claim 7, wherein said display means is an X-Y recorder.

* * * * *